US007879363B2

(12) United States Patent
Ritter

(10) Patent No.: US 7,879,363 B2
(45) Date of Patent: *Feb. 1, 2011

(54) METHOD FOR INCREASING LACTOSE TOLERANCE IN MAMMALS EXHIBITING LACTOSE INTOLERANCE

(75) Inventor: Andrew J. Ritter, Los Angeles, CA (US)

(73) Assignee: Ritter Pharmaceuticals, Inc., Los Angeles, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 12/013,161

(22) Filed: Jan. 11, 2008

(65) Prior Publication Data

US 2008/0112941 A1    May 15, 2008

Related U.S. Application Data

(63) Continuation of application No. 11/330,369, filed on Jan. 10, 2006, now abandoned, which is a continuation of application No. 09/346,479, filed on Jul. 1, 1999, now Pat. No. 7,029,702.

(60) Provisional application No. 60/091,971, filed on Jul. 7, 1998.

(51) Int. Cl.
*A61K 35/20*    (2006.01)

(52) U.S. Cl. .................. 424/535; 424/93.4; 424/93.44; 424/93.45; 426/43

(58) Field of Classification Search ...................... None
See application file for complete search history.

(56) References Cited

U.S. PATENT DOCUMENTS

| 3,627,583 | A | 12/1971 | Troy et al. |
| 5,219,842 | A | 6/1993 | Okada et al. |
| 5,709,857 | A | 1/1998 | Morelli et al. |
| 5,744,134 | A | 4/1998 | Paul |
| 5,895,648 | A | 4/1999 | Cavaliere Vesely et al. |
| 5,952,021 | A | 9/1999 | Santus |
| 5,952,205 | A | 9/1999 | Catani et al. |
| 6,093,425 | A | 7/2000 | Kamarei |
| 6,221,350 | B1 | 4/2001 | Brown et al. |
| 6,241,983 | B1 | 6/2001 | Paul et al. |
| 6,423,833 | B1 | 7/2002 | Catani et al. |
| 6,468,525 | B1 | 10/2002 | Watson et al. |
| 6,471,999 | B2 | 10/2002 | Couzy et al. |
| 6,706,287 | B2 | 3/2004 | Ranganathan et al. |
| 6,797,266 | B2 | 9/2004 | Naidu |
| 6,835,376 | B1 | 12/2004 | Neeser et al. |
| 6,929,793 | B2 | 8/2005 | Spivey-Krobath et al. |
| 6,960,341 | B2 | 11/2005 | Viscomi et al. |
| 7,029,702 | B2 | 4/2006 | Ritter |
| 7,101,553 | B2 | 9/2006 | Haschke et al. |
| 7,101,565 | B2 | 9/2006 | Monte |
| 7,172,777 | B2 | 2/2007 | Schmitt et al. |
| 7,195,906 | B2 | 3/2007 | Collins et al. |
| 2002/0034496 | A1 | 3/2002 | Ritter |
| 2003/0147995 | A1 | 8/2003 | Koss et al. |
| 2004/0005305 | A1 | 1/2004 | Spivey-Krobath et al. |
| 2004/0161422 | A1 | 8/2004 | Ranganathan |
| 2005/0074442 | A1 | 4/2005 | Ranganathan |
| 2005/0079244 | A1 | 4/2005 | Giffard et al. |
| 2006/0093592 | A1 | 5/2006 | Cheruvanky et al. |
| 2006/0104965 | A1 | 5/2006 | Ritter |
| 2006/0141097 | A1 | 6/2006 | Guo |
| 2006/0165670 | A1 | 7/2006 | Beer et al. |
| 2007/0196439 | A1 | 8/2007 | Catani et al. |
| 2008/0112942 | A1 | 5/2008 | Farmer et al. |
| 2008/0126195 | A1 | 5/2008 | Ritter |
| 2008/0193485 | A1 | 8/2008 | Gorbach et al. |
| 2008/0233092 | A1 | 9/2008 | Ritter |

FOREIGN PATENT DOCUMENTS

| DE | 20202562 U1 | 5/2002 |
| DE | 202005009120 U1 | 11/2005 |
| EP | 0474230 A1 | 3/1992 |
| EP | 0199535 B2 | 11/1995 |
| EP | 1195095 A2 | 4/2002 |
| EP | 1890553 B1 | 8/2008 |
| JP | 60-078540 | 5/1985 |
| KR | 10-2003-0064030 | 7/2003 |
| WO | WO 91/17672 A1 | 11/1991 |
| WO | WO 00/61155 A1 | 10/2000 |
| WO | WO 02/080946 A1 | 10/2002 |
| WO | WO 02/102168 A1 | 12/2002 |
| WO | WO 03/041512 A1 | 5/2003 |
| WO | WO 03/090546 A1 | 11/2003 |
| WO | WO 2004/067013 A1 | 8/2004 |
| WO | WO 2004/093571 A1 | 11/2004 |
| WO | WO 2004/098622 A2 | 11/2004 |

(Continued)

OTHER PUBLICATIONS

Arunachalam, et al. Role of Bifidobacteria in nutrition, medicine and technology. Nutrition Research. 1999; 19(10):1559-1597.

(Continued)

*Primary Examiner*—Susan C Hoffman
(74) *Attorney, Agent, or Firm*—Wilson Sonsini Goodrich & Rosati PC

(57) ABSTRACT

The method for increasing lactose tolerance in subjects exhibiting lactose intolerance symptoms implements a protocol where the subjects ingest a gradually increasing amount of lactose containing product over a six week period. At various points during the six week period the subject ingests the lactose containing product once a day and then twice a day. The lactose containing product can be in liquid form, such as for example, milk, and is preferably in a powder form which is taken either by ingesting capsules having the lactose powder or in a granular form mixed with water or other non-lactose containing liquid. At the end of the six week period, the subject's tolerance for lactose containing products is substantially increased, with the potential of eliminating the subject's lactose intolerant behavior indefinitely.

50 Claims, No Drawings

FOREIGN PATENT DOCUMENTS

| | | |
|---|---|---|
| WO | WO 2004/098622 A3 | 3/2005 |
| WO | WO 2006/113027 A2 | 10/2006 |
| WO | WO 2007/023226 A2 | 3/2007 |
| WO | WO 2007/023226 A3 | 6/2007 |
| WO | WO 2007/125558 A1 | 11/2007 |
| WO | WO 2006/113027 A3 | 12/2007 |
| WO | WO 2008/091756 A1 | 7/2008 |

OTHER PUBLICATIONS

Bartram, et al. Does yogurt enriched with *Bifidobacterium longum* affect colonic microbiology and fecal metabolites in health subjects? Am J Clin Nutr. Feb. 1994;59(2):428-32.

Bond, et al. Colonic conservation of malabsorbed carbohydrates. Gastroenterology, 78, 444-447, 1980.

Briet, et al. Improved clinical tolerance to chronic lactose ingestion in subjects with lactose intolerance: a placebo effect? Gut, 41, 632-635, 1997.

Broussalian, et al. Influence of lactose concentration of milk and yogurt on growth rate of rats. J Dairy Science, 66 (3), 438-443, 1983.

Collins, et al. Proximate, Nutritional and Microbiological Analyses of Milk-Sweet Potato Mixtures Fermented with Yogurt Bacteria. Journal of Food Science. 1991; 56:682-684.

Ekstrom, et al. Effects of a diet containing 40% dried whey on the performance and lactase activities in the small intestine and cecum of Hampshire and Chester white pigs. Journal of Animal Science, 42, 106-113, 1976.

Ekstrom, et al. Effect of diets containing dried whey on the lactase activity of the small intestinal mucosa and the contents of the small intestine and cecum of the pig. Journal of Nutrition, 105, 851-860, 1975.

Engstrom, et al. Intestinal disaccharidase activities of three breeds of swine. Journal of Animal Science, 48, 1349-1356, 1979.

Gibson, et al. Enrichment of bifidobacteria from human gut contents by oligofructose using continuous culture. FEMS Microbiol Lett. May 1, 1994;118(1-2):121-127.

Gibson, et al. Selective stimulation of bifidobacteria in the human colon by oligofructose and inulin. Gastroenterology. Apr. 1995;108(4):975-82.

Gomes, et al. *Bifidobacterium* spp. and *Lactobacillus acidophilus*: biological, biochemical, technological and therapeutical properties relevant for use as probiotics. Trends in Food Science and Technology. 1999; 10:139-157.

He, et al. Colonic fermentation may play a role in lactose intolerance in humans. Journal of Nutrition, 136, 58-63, 2006.

Hertzler, et al. Fecal hydrogen production and consumption measurements: response to daily lactose ingestion by lactose maldigesters. Digestive Diseases and Sciences, 42 (2), 348-353, 1997.

Johnson, et al. Adaptation of lactose maldigesters to continued milk intakes. American Journal of Clinical Nutrition. 58, 879-881, 1993.

Kim, et al. In vitro measurements of the lactase activity and the fermentation products of lactose in the cecal and colonic contents of rats fed a control or 30% lactose diet. Journal of Nutrition, 109, 856-63, 1979.

Landon, et al. A double-blind test of the ability of lactagen formula to reduce symptoms of lactose intolerance. Lactagen Clinical Study. Published Jun. 28, 2005 at www.lactagen.com.

Landon, et al. A randomized controlled trial to evaluate effectiveness of a pre- and probiotic formula to treat patients with self-reported severe intolerance to dairy products. Poster presentation at FASEB meeting, Apr. 1-5, 2006. San Francisco, CA. (Poster).

Landon, et al. A randomized trial of a pre- and probiotic formula to reduce symptoms of dairy products in patients with dairy intolerance. Meeting Abstract. FASEB meeting, Apr. 1-5, 2006. San Francisco, CA. Page A1053.

Martini, et al. Strains and species of lactic acid bacteria in fermented milks (yogurts): effect on in vivo lactose digestion. Am J Clin Nutr. Dec. 1991;54(6):1041-6.

Metagenics' Product Catalog—Science-based nutraceuticals for improved patient health. Published Oct. 15, 2006 at www.metagenics.com.

Perman, et al. Role of pH in production of hydrogen from carbohydrates by colonic bacterial flora. Journal of Clinical Investigation. 67, 643-650, 1981.

Pribila, et al. Improved lactose digestion and intolerance among African-American adolescent girls fed a dairy-rich diet. Journal of the American Dietetic Association, 100 (5), 524-528, 2000.

Roberfroid, M. Prebiotics and probiotics: are they functional foods? Am J Clin Nutr. Jun. 2000;71(6 Suppl):1682S-7S.

Siddons, et al. The influence of the intestinal mciroflora on disaccharidase activities in the chick. British Journal of Nutrition, 27, 101-112, 1972.

Wang, et al. Effects of the in vitro fermentation of oligofructose and inulin by bacteria growing in the human large intestine. J Appl Bacteriol. Oct. 1993;75(4):373-80.

Wen, et al. Lactose feeding in lactose-intolerant monkeys. American Journal of Clinical Nutrition. 26, 1224-1228, 1973.

Zhong, et al. The role of colonic microbiotica in lactose intolerance. Digestive Diseases and Sciences, 49 (1), 78-83, 2004.

DFO-Nutrition Services: Spotlight for Sep. 1995. Lactose Intolerance: Common Concerns. Available at http://www.milk.org/spotsept.htm. Accessed May 17, 1999.

Gilat, et al. Lactase in man: a nonadaptable enzyme. Gastroenterology. Jun. 1972;62(6):1125-7.

Hertzler, et al. Colonic adaptation to daily lactose feeding in lactose maldigesters reduces lactose intolerance. Am J Clin Nutr. Aug. 1996;64(2):232-6.

Kim, et al. *Lactobacillus acidophilus* as a dietary adjunct for milk to aid lactose digestion in humans. J Dairy Sci. 1983; 66(5):959-66.

Kretchmer, N. Lactose and lactase—a historical perspective. Gastroenterology. Dec. 1971;61(6):805-13.

Martini, et al. Lactose digestion from yogurt: influence of a meal and additional lactose. Am J Clin Nutr. 1991; 53(5):1253-1258.

National Digestive Disease. Lactose Intolerance. Available at http://www.niddk.nih.gov/health/digest/pubs/lactose/lactose.htm. Accessed May 17, 1999.

Onwulata, et al. Relative efficiency of yogurt, sweet acidophilus milk, hydrolyzed-lactose milk, and a commercial lactase tablet in alleviating lactose maldigestion. Am J Clin Nutr. 1989; 49(6):1233-1237.

Suarez, et al. A comparison of symptoms after the consumption of milk or lactose-hydrolyzed milk by people with self-reported severe lactose intolerance. N Engl J Med. Jul. 6, 1995;333(1):1-4.

Manzi, et al. New functional milk-based products in the Italian market. Food Chemistry. 2007; 104(2):808-813.

Hamilton, Great Srnokies Diagnostic Laboratory Application Guide, Lactose Intolerance Breath Test, Asheville, 1996.

McBean, Dairy Council Digest. National Dairy Council: Rosemont, IL, Mar./Apr. 1994, vol. 65, #2.

Great Smokies Diagnostic Laboratory. Was it something you ate or drank? http://www.gsdl.com/NP/services/patbroch/actpb.html, 1995-6.

National Digestive Diseases Information Clearinghouse. Lactose Intolerance. http://niddk.nih.gov/LactoseIntolerance/LactoseIntolerance.html, Apr. 1994.

Cure Your lactose Intolerance!, advertisement for the Daily Bruin Classified, Monday, Jan. 12, 1998, p. 39.

International search report dated Feb. 2, 2010 for PCT Application No. US2009/03834.

International search report dated Mar. 31, 2006 for PCT Application No. US2005/26095.

International search report dated Jun. 14, 2007 for PCT Application No. US2007/061464.

Office action dated Jan. 26, 2010 for U.S. Appl. No. 11/670,198.

Office action dated Feb. 3, 2010 for U.S. Appl. No. 12/055,936.

Office action dated Mar. 8, 2001 for U.S. Appl. No. 09/346,479.

Office action dated Jul. 11, 2007 for U.S. Appl. No. 11/330,369.

Office action dated Aug. 5, 2009 for U.S. Appl. No. 12/055,936.

Office action dated Sep. 28, 2000 for U.S. Appl. No. 09/346,479.

Office action dated Nov. 29, 2001 for U.S. Appl. No. 09/346,479.

Office action dated Dec. 30, 2008 for U.S. Appl. No. 12/055,936.

METHOD FOR INCREASING LACTOSE TOLERANCE IN MAMMALS EXHIBITING LACTOSE INTOLERANCE

CROSS-REFERENCES

This application is a continuation of U.S. patent application Ser. No. 11/330,369, filed Jan. 10, 2006, now abandoned, which is a continuation of U.S. patent application Ser. No. 09/346,479, filed Jul. 1, 1999, now U.S. Pat. No. 7,029,702, which claims benefit to Provisional Application No. 60/091,971, filed on Jul. 7, 1998, all of which are incorporated by reference herein in their entirety.

FIELD OF THE INVENTION

The present invention relates to a method for increasing lactose tolerance in individuals or mammals who exhibit lactose intolerant symptoms.

BACKGROUND OF THE INVENTION

Lactose Intolerance, or otherwise referred to as lactose maldigestion, is the inability to digest a significant amount of lactose, derived from a deficiency of the lactase enzyme in the small intestines. Lactose is the natural sugar in milk and milk products of all mammals. Lactase is the enzyme which splits the milk sugar lactose into its components (i.e., glucose and galactose), and also breaks down the milk sugar into smaller forms that can be processed into the bloodstream. The lactase enzyme is necessary for mammals to digest lactose.

There is an important distinction between lactose intolerance and milk allergies. Lactose intolerance is the inability of the body to digest lactose containing products due to a deficiency in the lactase enzyme. A milk allergy, however, is a sensitivity to the protein in milk, which involves the immune system and does not relate to a deficiency of the lactase enzyme. In humans, a milk allergy is usually experienced only by infants.

Generally, humans develop lactose intolerance from a primary or secondary cause. The primary cause is an onset loss of lactase that is a permanent condition. This occurs at a variable period after the weaning period. The primary cause is also genetically determined. The secondary cause is generally a temporary condition that occurs as a result of another disease or event that damages the lining of the small intestine where lactase is active. This is usually caused by an acute diarrheal disease, parasitic infection, Crohn's disease, celiac disease, gastrointestinal surgery, or the intake of certain medications.

In addition to the primary and secondary causes, certain human ethnic and racial populations have more of a predisposition for lactose intolerance. In these populations, social and cultural habits and attitudes influence lactose intolerance. Lactose activity can also decrease with age in certain ethnic and racial populations, including those populations which have origins in Europe, the African plains, and the Siberian Steppes. Humans who are most likely to have or develop lactose intolerance include those of Asian, Middle Eastern, North American, African, and Latin American descent.

According to several sources, there are 30 to 50 million people in the world who are lactose intolerant. In the 1960's and 1970's, it was reported that 70% of the adults in the world had lactose intolerance. In 1995, is was reported that 75% of the adults in the world and 25% of the adults in the U.S. were categorized as being lactose intolerant. In 1994, it was reported that 75% of African Americans and Native Americans and 90% of Asian Americans had lactose intolerance. It has also been reported that 30% of adults who are mostly North Western and North American descendants of the Europeans, have adapted to high lactase activity into adulthood. Research concludes that this adaptation is genetically controlled, permanent and related to a long tradition of milk and milk products consumption in these regions of the world.

Lactose intolerance can be tested either indirectly or directly. There are three main ways to test by the indirect method: a hydrogen breath test, a stool acidity test, or a blood glucose test. In the hydrogen breath test, the breath is measured to determine the amount of hydrogen produced after consuming a measured amount of lactose, typically 15 g. The lactose is consumed by drinking a lactose mixture, and the subject exhales into a vacuum-sealed collection tube at three one hour time intervals. A high level of hydrogen in the breath indicates an improper digestion of lactose. In a stool test, the stool is tested to determine the amount of acid. In a blood glucose test, the blood is tested to determine the amount of glucose (sugar) content after administering a predetermined amount of lactose-containing product to the subject. The direct method measures lactose activity in a mucosal biopsy specimen.

If an individual suspects that he has lactose intolerance, it is potentially harmful for him to restrict his diet since it may result in a nutrition shortage or a failure to detect a more serious disease. Milk and other dairy products are major sources for nutrition in the basic American diet. The primary nutrients in milk are protein, calcium, riboflavin, vitamin A, and vitamin D. Calcium is an important part of the recommended daily allowances of vitamins and minerals and any deficiency therein can lead to osteoporosis.

When an individual has an allergic reaction to milk, there are several different resulting symptoms depending on the age of the individual. For young adults and adults, symptoms include bloating, nausea, cramps, and diarrhea, while the symptoms in infants are diarrhea, dehydration, malnutrition, and potentially death. Some of the symptoms vary based on the level of tolerance the person has, the amount and type of lactose consumed, or the remainder of the person's diet.

Lactose is not digested when the amount of lactose consumed exceeds the lactase enzyme capacity of the small intestine. Instead, excess undigested lactose passes through the small intestines into the large intestine where it is fermented by a bacteria called colinic flora. The fermentation of the lactose in the large intestine produces hydrogen and methane which can lead to bloating, gas, and diarrhea. These symptoms are caused by a very low activity of lactase in the intestines.

The use of lactase tablets which are generally available, help lactose intolerant people digest milk and milk products. Each lactase tablet typically hydrolyzes up to 99% of the ingested lactose within 24 hours, and is designed to be ingested with the lactose containing food.

Young children who have lactose intolerance are very rare. The amount of lactase enzyme a body produces generally reaches a maximum immediately after birth and then decreases in the majority of people after their body adjusts during the ages of 3-15. A stool test is used to test lactose intolerance in young children. For young children, the breath test is not as accurate because they usually have a tendency to get dehydrated which can cause diarrhea.

The reasons for an onset of lactose intolerance are generally unknown. However, there is a general belief that by consuming small amounts of lactose frequently over a period of time, lactose intolerance can be improved. Whole milk and chocolate milk appear to be tolerated better than low fat milk because the fat content of whole milk and chocolate milk slows the rate of gastric emptying. Many lactose intolerant people can have at least 8 oz of milk. Also, many lactose intolerant people can have hard cheeses because during manufacturing most of the lactose is removed with the whey. During the aging of the cheeses, the remaining lactose is converted to lactic acid and other products. As a result, most aged cheeses have little to no lactose. Some of such firm cheeses include cheddar, Swiss and mozzarella. Another product that lactose intolerant people can tolerate is yoghurt, with live culture bacteria in it. Having yoghurt with a non-fermented dairy product can improve lactose digestion.

People typically have different symptoms of lactose intolerance. Lactose intolerance may also be psychologically induced. There are also many different variations of lactose intolerance depending on the individual. For example, some individuals cannot have cheese, melted cheese, plain milk, or warm dairy containing products like milk in coffee, while others cannot have any dairy products at all. Also, most lactose intolerant people are limited as to the amount of special "lactose free" foods they can eat that have been manufactured by specific companies. Some examples of these "lactose free" foods are: Mocha Mix ice cream, Tofutti ice cream and ice cream sandwiches, LACTAID® brand milk, Formagg cheese, Tofutti "Better than Cream Cheese", margarine, and live cultured yoghurt. The only problem with all these products is that they are not readily available everywhere.

SUMMARY OF THE INVENTION

The present invention provides a method for increasing the lactose tolerance of mammals exhibiting lactose intolerance symptoms. In accordance with the invention, a six-week protocol is employed during which a subject ingests gradually increasing amounts of a lactose-containing product. On the first and second days of the protocol, the subject also ingests a predetermined amount of a live culture bacteria containing compound, such as yoghurt. Toward the end of the six-week period, the subject starts ingesting other lactose-containing products while continuing to ingest the predetermined amount of lactose containing product. By the conclusion of the six-week protocol, the subject's tolerance for lactose-containing products is significantly increased, and in some cases, the subject no longer experiences any lactose intolerance or the symptoms associated therewith.

In accordance with a preferred embodiment of the invention, the lactose-containing product is administered to the subject is in the form of a lactose powder. The lactose powder can be provided within an ingestable capsule or in granular form which is measured out and added to the subject meal or drink.

The various features of novelty which characterize the invention are pointed out with particularity in the claims annexed to and forming a part of the disclosure.

DETAILED DESCRIPTION OF PREFERRED EMBODIMENTS

According to a first embodiment of the invention, a predetermined first dose of a liquid form of a lactose-containing product, such as, for example milk, is administered to the subject once each day in gradually increasing amounts during the course of a six-week period. On the first and second days, a predetermined amount of a substance containing live cultured bacteria, such as yoghurt, is administered to the subject with the dose of lactose-containing product. Subsequently, during the six-week period, a second dose of the liquid form of lactose, in addition to the first dose, is administered to the subject at a second time during each day.

An example of this dosing regimen is shown below in Table 1. On the first day, the subject ingests 8 ounces of live culture bacteria yoghurt with 1 tablespoon of milk with dinner. On day 2, the amount of yoghurt ingested is reduced to 4 ounces and the amount of milk administered remains the same. On day 3, administration of the yoghurt is ceased, and the milk dose remains at one tablespoon. During days 4 through 18, the amount of milk ingested with dinner is increased by one tablespoon each day until 16 tablespoons are reached on day 18. On day 19, a second dose, 1 tablespoon, of milk is ingested in the morning with breakfast and 16 tablespoons of milk are ingested with dinner. From day 16 until day 34, the subject continues to ingest 16 tablespoons of milk with dinner. The morning dose is increased daily at a rate of 1 tablespoon per day so that by day 34 the subject ingests 16 tablespoons of milk with breakfast and 16 tablespoons with dinner. On day 35, the subject discontinues ingesting the lactose containing product in tablespoon doses and begins ingesting milk, starting with 9 ounces in the morning and 9 ounces in the evening with the meals. The amount of milk is increased an ounce each day so that by day 38, the subject ingests 12 ounces of milk with both breakfast and dinner. On day 39, the subject discontinues the milk intake and instead ingests 1 ounce of cheese. The amount of cheese is increased to 2 ounces on day 40. By day 41, the subject's lactose intolerance has been completely eliminated, and the subject is free to eat any dairy product of his choice.

TABLE 1

| Week | Day | PM-Dosage | AM-Dosage |
|---|---|---|---|
| 1 | 1 | 1 tbs + 8 oz yogurt | |
| 1 | 2 | 1 tbs + 4 oz yogurt | |
| 1 | 3 | 1 tbs | |
| 1 | 4 | 2 tbs | |
| 1 | 5 | 3 tbs | |
| 1 | 6 | 4 tbs | |
| 1 | 7 | 5 tbs | |
| 2 | 8 | 6 tbs | |
| 2 | 9 | 7 tbs | |
| 2 | 10 | 8 tbs | |
| 2 | 11 | 9 tbs | |
| 2 | 12 | 10 tbs | |
| 2 | 13 | 11 tbs | |
| 2 | 14 | 12 tbs | |
| 3 | 15 | 13 tbs | |
| 3 | 16 | 14 tbs | |
| 3 | 17 | 15 tbs | |
| 3 | 18 | 16 tbs | |
| 3 | 19 | 16 tbs | 1 tbs |
| 3 | 20 | 16 tbs | 2 tbs |
| 3 | 21 | 16 tbs | 3 tbs |
| 4 | 22 | 16 tbs | 4 tbs |
| 4 | 23 | 16 tbs | 5 tbs |
| 4 | 24 | 16 tbs | 6 tbs |
| 4 | 25 | 16 tbs | 7 tbs |
| 4 | 26 | 16 tbs | 8 tbs |
| 4 | 27 | 16 tbs | 9 tbs |
| 4 | 28 | 16 tbs | 10 tbs |
| 5 | 29 | 16 tbs | 11 tbs |
| 5 | 30 | 16 tbs | 12 tbs |
| 5 | 31 | 16 tbs | 13 tbs |
| 5 | 32 | 16 tbs | 14 tbs |
| 5 | 33 | 16 tbs | 15 tbs |
| 5 | 34 | 16 tbs | 16 tbs |
| 5 | 35 | 9 oz milk | 9 oz milk |
| 6 | 36 | 10 oz milk | 10 oz milk |
| 6 | 37 | 11 oz milk | 11 oz milk |
| 6 | 38 | 12 oz milk | 12 oz milk |

TABLE 1-continued

| Week | Day | PM-Dosage | AM-Dosage |
|---|---|---|---|
| 6 | 39 | Cheese 1 oz | |
| 6 | 40 | Cheese 2 oz | |
| 6 | 41 | lactose tolerance achieved | |
| 6 | 42 | | |

Table 1 shows an exemplary six-week protocol however, the actual days on which the doses are changed and the quantity of the doses can be modified according to the subject and his specific reactions without departing from the scope of the invention. For example, the subject may be capable of ingesting more than 5 tablespoons of milk by day 7, and could therefore increase it to 6 tablespoons on day 7, and so on. Alternatively, the subject may find that the transition from 5 tablespoons on day 7 (which he is capable of ingesting without any adverse effect) to 6 tablespoons on day 8 may result in an adverse effect. As such, the subject may revert back to the 5 tablespoon dose and continue that dose for a longer period than originally prescribed (e.g., 2 or more days) before increasing the dosage again. The same variable modification to the protocol applies to the lactose powder protocol described below with reference to Table 2.

In another embodiment of the present invention, the lactose containing product administered to the subject is a pure powder lactose that is contained in an ingestable capsule or an equivalent amount in a loose granular form mixed with water or other non-lactose containing product. An example of the powder lactose regimen is shown in Table 2. In Table 2, the designation "s" refers to a 1 zero sized capsule filled with 0.8 grams of pure powder lactose (which is equivalent to 1 tablespoon of milk), and "m" refers to a double sized zero capsule filled with 1.6 grams of pure lactose powder. The amount of lactose ingested in any period in accordance with the regimen shown in Table 2 is identical to that of the regimen shown in Table 1 except that the form of the lactose is different.

TABLE 2

| Week | Day | PM-Dosage | AM-Dosage |
|---|---|---|---|
| 1 | 1 | s + 8 oz yogurt | |
| 1 | 2 | s + 4 oz yogurt | |
| 1 | 3 | s | |
| 1 | 4 | m | |
| 1 | 5 | m + s | |
| 1 | 6 | 2 m | |
| 1 | 7 | 2 m + s | |
| 2 | 8 | 3 m | |
| 2 | 9 | 3 m + s | |
| 2 | 10 | 4 m | |
| 2 | 11 | 4 m + s | |
| 2 | 12 | 5 m | |
| 2 | 13 | 5 m + s | |
| 2 | 14 | 6 m | |
| 3 | 15 | 6 m + s | |
| 3 | 16 | 7 m | |
| 3 | 17 | 7 m + s | |
| 3 | 18 | 8 m | |
| 3 | 19 | 8 m | s |
| 3 | 20 | 8 m | m |
| 3 | 21 | 8 m | m + s |
| 4 | 22 | 8 m | 2 m |
| 4 | 23 | 8 m | 2 m + s |
| 4 | 24 | 8 m | 3 m |
| 4 | 25 | 8 m | 3 m + s |
| 4 | 26 | 8 m | 4 m |
| 4 | 27 | 8 m | 4 m + s |

TABLE 2-continued

| Week | Day | PM-Dosage | AM-Dosage |
|---|---|---|---|
| 4 | 28 | 8 m | 5 m |
| 5 | 29 | 8 m | 5 m + s |
| 5 | 30 | 8 m | 6 m |
| 5 | 31 | 8 m | 6 m + s |
| 5 | 32 | 8 m | 7 m |
| 5 | 33 | 8 m | 7 m + s |
| 5 | 34 | 8 m | 8 m |
| 5 | 35 | 9 oz milk | 9 oz milk |
| 6 | 36 | 10 oz milk | 10 oz milk |
| 6 | 37 | 11 oz milk | 11 oz milk |
| 6 | 38 | 12 oz milk | 12 oz milk |
| 6 | 39 | Cheese 1 oz | |
| 6 | 40 | Cheese 2 oz | |
| 6 | 41 | lactose tolerance achieved | |
| 6 | 42 | | |

The method of the present invention was initially tested on the applicant and after obtaining positive results, additional testing was performed on 10 adult human subjects. Five of the subjects followed the liquid protocol of Table 1, while the other five followed the capsule protocol of Table 2. Some of the test subjects experienced mild gas and discomfort at various points early in the program. At the end of the protocol; eight of the ten subjects tested considered themselves "cured" of lactose intolerance. One of the two who did not achieve the desired results interrupted the protocol by stopping in the middle and subsequently tried to restart a week later. This subject attributed his failure to stopping in the middle and to ingesting other foods such as creamed spinach, pizza, frozen yoghurt, chocolate and other lactose containing foods during the protocol period. The other did not finish the six week protocol. The subjects who strictly followed the six-week protocol program for increasing lactose tolerance increased their lactose tolerance to a point where they are free to enjoy any lactose containing food of their choice.

Although the doses shown here have been used and tested, variations in the doses and timing in which they are administered can still result in an effective treatment for increasing tolerance for lactose containing products. For example, the presented doses have been tested on adult subjects. Thus, when applying the protocol of the present invention to younger subjects, the weight of the subject might be a consideration. For example, a subject weighing 50 pounds may not require, and may not be capable of tolerating, the doses set forth in Tables 1 and 2 at the prescribed time in the protocol. As such, the dose administered to the subject may be proportionally scaled down based on his weight. Although the two doses are disclosed as being administered with breakfast and dinner, alternatively the order of the doses maybe switched, or may be administered at other times of the day with meals such as lunch or snacks (or conceivably with no meals). Although the invention has been described for use in humans, it is also capable of being administered to other mammals.

The invention is not limited by the embodiments described above which are presented as examples only but can be modified in various ways within the scope of protection defined by the appended patent claims.

What is claimed is:

1. A method for increasing lactose tolerance in a subject experiencing lactose intolerance comprising:
   administering a first dosage of a lactose containing product to the subject each day for a first predetermined number of days;

administering a predetermined amount of live cultured bacteria to the subject each day in conjunction with said first dosage of said lactose containing product, said administering of the live cultured bacteria commencing on the first day of the first predetermined number of days and continuing over a second predetermined number of days;

increasing the first dosage of the lactose containing product over the course of the first predetermined number of days;

administering a second dosage of the lactose containing product to the subject each day starting at a first predetermined point during the first predetermined number of days; and increasing the second dosage of the lactose containing product over the course of the first predetermined number of days, wherein said second dosage is administered at a time of the day different than when said first dosage is administered, wherein said method decreases one or more symptoms of lactose intolerance in said subject following the end of the first predetermined number of days, wherein said one or more symptoms of lactose intolerance comprises diarrhea, cramps, or nausea.

2. The method set forth in claim 1, wherein said first predetermined number of days is about 34 days.

3. The method set forth in claim 2, wherein said second predetermined number of days is about two days.

4. The method set forth in claim 1, wherein said first predetermined point is about the nineteenth day of said first predetermined number of days.

5. The method set forth in claim 1, wherein the lactose containing product is milk.

6. The method set forth in claim 1, wherein the lactose containing product comprises lactose powder.

7. The method set forth in claim 6, wherein the lactose powder is in granular form.

8. The method set forth in claim 6, wherein the lactose powder is contained in capsules.

9. The method set forth in claim 5, wherein said administering said first dosage of the lactose containing product comprises administering to said subject about 1 tablespoon of milk for days 1-3 of said first predetermined number of days; wherein said increasing said first dosage comprises increasing the amount of milk administered to said subject at a rate of 1 additional tablespoon for each day beginning with day 4 such that by about day 18 of said first predetermined number of days said amount of said first dosage administered to said subject is about 16 tablespoons of milk.

10. The method set forth in claim 9, wherein said administering said second dosage of said lactose containing product comprises administering to said subject about 1 tablespoon of milk starting on about day 19 of said first predetermined number of days; wherein said increasing said second dosage comprises increasing the amount of milk administered to said subject at a rate of 1 additional tablespoon of milk for each day such that by about day 34 of said first predetermined number of days said second dosage is about 16 tablespoons of milk.

11. The method set forth in claim 10, further comprising:
discontinuing administering of the first and second dosage of said milk at the end of said first predetermined number of days; and
administering to the subject a second lactose containing product in a predetermined amount twice each day beginning the day after the end of said first predetermined number of days and continuing for four days;
wherein said predetermined amount of said second lactose containing product comprises about 9 ounces of milk, said predetermined amount of said second lactose containing product increasing at a rate of 1 ounce each day for three days such that on the third day said predetermined amount of said second lactose containing product administered comprises about 12 ounces of milk.

12. The method set forth in claim 7, wherein said administering said first dosage of said lactose containing product comprises administering to said subject about 0.8 grams of lactose powder for days 1-3 of said first predetermined number of days, wherein said increasing said first dosage comprises increasing the amount of lactose powder administered to said subject at a rate of about 0.8 additional grams of lactose powder for each day such that by about day 18 of said first predetermined number of days said amount of said first dosage administered to said subject is about 12.8 grams of lactose powder.

13. The method set forth in claim 12, wherein said administering said second dosage of said lactose containing product comprises administering to said subject about 0.8 grams of lactose powder starting on about day 19 of said first predetermined number of days, wherein said increasing said second dosage of said lactose containing product comprises increasing the amount of lactose powder administered to said subject at a rate of about 0.8 additional grams of lactose powder for each day such that by about day 34 of said first predetermined number of days said amount of said second dosage of said lactose containing product that is administered to said subject is about 12.8 grams of lactose powder.

14. The method set forth in claim 13, further comprising:
discontinuing administering of the first and second dosage of said lactose powder at the end of said first predetermined number of days; and
administering to the subject a second lactose containing product in a predetermined amount twice each day beginning the day after the end of said first predetermined number of days and continuing for four days;
wherein said predetermined amount of said second lactose containing product comprises about 9 ounces of milk, said second predetermined amount of said second lactose containing product increasing at a rate of 1 ounce each day for three days such that on the third day said predetermined amount of said second lactose containing product administered comprises about 12 ounces.

15. The method set forth in claim 11, further comprising discontinuing the administering of said second lactose containing product at the end of the four days and administering varying doses of cheese for two days thereafter with dinner.

16. The method set forth in claim 14, further comprising discontinuing the administering of said second lactose containing product at the end of the four days and administering varying doses of cheese for two days thereafter with dinner.

17. The method set forth in claim 1, wherein said steps of administering are performed without meals.

18. The method set forth in claim 1, wherein said steps of administering are performed in conjunction with meals.

19. The method set forth in claim 18, wherein said step of administering a first dosage is performed with dinner, said step of administering a second dosage is performed with breakfast.

20. The method set forth in claim 6, wherein said steps of administering are performed without meals.

21. The method set forth in claim 6, wherein said steps of administering are performed in conjunction with meals.

22. The method set forth in claim 21, wherein said step of administering a first dosage is performed with dinner, said step of administering a second dosage is performed with breakfast.

23. The method of claims 11 or 14, wherein said day after is about the thirty-fifth day after the start of said first predetermined number of days.

24. A method for increasing lactose tolerance in a subject experiencing lactose intolerance comprising:
administering a first dosage of a lactose containing product to the subject each day for a predetermined number of days;
administering a predetermined amount of live cultured bacteria to the subject in conjunction with said lactose containing product;
increasing the amount of said first dosage of the lactose containing product administered to said subject until a first predetermined point;
administering a second dosage of the lactose containing product to the subject each day starting at a second predetermined point; increasing the second dosage of the lactose containing product until the end of the predetermined number of days; wherein the first dosage of the lactose containing product is administered at a constant amount to said subject from said first predetermined point until the end of the predetermined number of days, wherein said second dosage is administered at a time of the day different than when said first dosage is administered, wherein said method decreases one or more symptoms of lactose intolerance in said subject following the end of the predetermined number of days, wherein said one or more symptoms of lactose intolerance comprises diarrhea, cramps, or nausea.

25. The method set forth in claim 24, wherein said predetermined number of days is about 34 days.

26. The method set forth in claim 24, wherein said first predetermined point is about the eighteenth day of said first predetermined number of days.

27. The method set forth in claim 24, wherein said second predetermined point is about the nineteenth day of said predetermined number of days.

28. The method set forth in claim 24, wherein the lactose containing product is milk.

29. The method set forth in claim 24, wherein the lactose containing product comprises lactose powder.

30. The method set forth in claim 29, wherein the lactose powder is in granular form.

31. The method set forth in claim 29, wherein the lactose powder is contained in capsules.

32. The method of claim 24, wherein said first dosage of a lactose containing product comprises about 1 tablespoon of milk for days 1-3 of said predetermined number of days, said amount of said first dosage of a lactose containing product increasing at a rate of 1 additional tablespoon for each day beginning with day 4 and continuing until said first predetermined point.

33. The method of claim 32, wherein said second dosage of a lactose containing product comprises about 1 tablespoon of milk on said second predetermined point, said amount of said second dosage of a lactose containing product increasing at a rate of 1 additional tablespoon of milk until said end of said predetermined number of days.

34. The method of claim 24, wherein said first dosage of a lactose containing product comprises about 0.8 grams of lactose powder for days 1-3 of said predetermined number of days, said amount of said first dosage of a lactose containing product increasing at a rate of 0.8 additional grams for each day beginning with day 4 and continuing until said first predetermined point.

35. The method of claim 32, wherein said second dosage of a lactose containing product comprises about 0.8 grams of lactose powder on said second predetermined point, said amount of said second dosage of a lactose containing product increasing at a rate of 0.8 grams of additional lactose powder until said end of said predetermined number of days.

36. The method of claim 24, further comprising: administering 9-12 ounces of milk twice a day at different time points to said subject for 1-4 days after said end of predetermined days.

37. The method set forth in claim 36, further comprising administering varying amounts of cheese to said subject for two days after cessation of the administration of said 9-12 ounces of milk.

38. The method set forth in claim 24, wherein said first and second dosages of a lactose containing product are administered without meals.

39. The method set forth in claim 24, wherein said first and second dosages of a lactose containing product are administered with meals.

40. The method set forth in claim 39, wherein said first dosage is administered with dinner, and said second dosage is administered with breakfast.

41. A method for increasing lactose tolerance in a subject experiencing lactose intolerance comprising the steps of:
administering a first dosage of a lactose containing product to the subject each day for a first predetermined number of days;
administering a predetermined amount of live cultured bacteria to the subject each day in conjunction with said administering the first dosage of said lactose containing product, said administering of the live culture bacteria commencing on the first day of the first predetermined number of days and continuing over a second predetermined number of days;
increasing the first dosage over the course of the first predetermined number of days;
administering a second dosage of the lactose containing product to the subject each day starting at a first predetermined point during the first predetermined number of days; and
increasing the second dosage over the course of the first predetermined number of days; wherein said first predetermined number of days is about 34 days; wherein said first predetermined point is about the nineteenth day of said first predetermined number of days; wherein said first dosage comprises about 0.8 grams of lactose containing product for days 1-3 of said first predetermined number of days, said first dosage increasing at a rate of about 0.8 additional grams for each day such that by about day 18 of said first predetermined number of days said first dosage is about 12.8 grams of lactose containing product; wherein said second dosage comprises about 0.8 grams of lactose containing product starting on about day 19 of said first predetermined number of days, said second dosage increasing at a rate of about 0.8 additional grams of lactose containing product for each day such that by about day 34 of said first predetermined number of days said second dosage is about 12.8 grams of lactose containing product, wherein said second dosage is administered at a time of the day different than when said first dosage is administered.

42. The method set forth in claim 41, wherein the lactose containing product comprises lactose powder.

43. The method set forth in claim 24, wherein the lactose powder is in granular form.

44. The method set forth in claim 43, wherein the lactose powder is contained in capsules.

45. The method of claim 41, further comprising: administering 9-12 ounces of milk twice a day at different time points to said subject for 1-4 days after said end of predetermined days.

46. The method set forth in claim 45, further comprising administering varying amounts of cheese to said subject for two days after cessation of the administration of said 9-12 ounces of milk.

47. The method set forth in claim 41, wherein said first and second dosages of a lactose containing product are administered without meals.

48. The method set forth in claim 41, wherein said first and second dosages of a lactose containing product are administered with meals.

49. The method set forth in claim 41, wherein said first dosage is administered with dinner, and said second dosage is administered with breakfast.

50. The method of claims 41, wherein said method decreases one or more symptoms of lactose intolerance in said subject following the end of the predetermined number of days, wherein said one or more symptoms of lactose intolerance comprises diarrhea, cramps, or nausea.

* * * * *

UNITED STATES PATENT AND TRADEMARK OFFICE
CERTIFICATE OF CORRECTION

| | | |
|---|---|---|
| PATENT NO. | : 7,879,363 B2 | Page 1 of 1 |
| APPLICATION NO. | : 12/013161 | |
| DATED | : February 1, 2011 | |
| INVENTOR(S) | : Andrew J. Ritter | |

It is certified that error appears in the above-identified patent and that said Letters Patent is hereby corrected as shown below:

Column 11, line 1, the claim reference numeral "24" should read --42--.

Signed and Sealed this
Nineteenth Day of April, 2011

David J. Kappos
*Director of the United States Patent and Trademark Office*